US011666565B2

(12) United States Patent
Lan

(10) Patent No.: US 11,666,565 B2
(45) Date of Patent: Jun. 6, 2023

(54) TREATMENT OF CANCER USING A SMAD3 INHIBITOR

(71) Applicant: The Chinese University of Hong Kong, Hong Kong SAR (CN)

(72) Inventor: Hui Yao Lan, Hong Kong SAR (CN)

(73) Assignee: The Chinese University of Hong Kong, Hong Kong SAR (CN)

( * ) Notice: Subject to any disclaimer, the term of this patent is extended or adjusted under 35 U.S.C. 154(b) by 0 days.

(21) Appl. No.: 15/063,661

(22) Filed: Mar. 8, 2016

(65) Prior Publication Data

US 2016/0279123 A1    Sep. 29, 2016

Related U.S. Application Data

(63) Continuation of application No. 13/779,090, filed on Feb. 27, 2013, now abandoned.

(60) Provisional application No. 61/719,114, filed on Oct. 26, 2012.

(51) Int. Cl.
| | |
|---|---|
| *A61K 31/4725* | (2006.01) |
| *A61K 31/713* | (2006.01) |
| *A61K 31/7105* | (2006.01) |
| *A61P 35/00* | (2006.01) |
| *A61K 31/7088* | (2006.01) |
| *A61K 38/00* | (2006.01) |
| *A61K 39/395* | (2006.01) |
| *A61K 9/00* | (2006.01) |

(52) U.S. Cl.
CPC ........ *A61K 31/4725* (2013.01); *A61K 9/0019* (2013.01); *A61K 31/7088* (2013.01); *A61K 31/713* (2013.01); *A61K 31/7105* (2013.01); *A61K 38/00* (2013.01); *A61K 39/3955* (2013.01); *A61P 35/00* (2018.01)

(58) Field of Classification Search
CPC .............. A61K 31/4725; A61K 31/713; A61K 31/7105; A61K 9/0019; A61K 31/7088; A61K 38/00; A61P 35/00
See application file for complete search history.

(56) References Cited

U.S. PATENT DOCUMENTS

| | | | |
|---|---|---|---|
| 6,013,788 A | 1/2000 | Brett et al. | |
| 6,239,114 B1 | 5/2001 | Guthrie et al. | |
| 2003/0139366 A1 | 7/2003 | Roberts | |
| 2004/0176390 A1 | 9/2004 | Blumberg et al. | |
| 2005/0014942 A1* | 1/2005 | Maruyama | A61K 31/404 544/183 |
| 2005/0276802 A1 | 12/2005 | Adams et al. | |

FOREIGN PATENT DOCUMENTS

| | | |
|---|---|---|
| EP | 2 397 157 A1 | 12/2011 |
| WO | 2004/068143 A1 | 8/2004 |
| WO | 2008/022467 A1 | 2/2008 |
| WO | 2008/046964 A2 | 4/2008 |
| WO | 2009/151600 A2 | 12/2009 |

OTHER PUBLICATIONS

Mohammad et al. (Cancer Research, 2010, 71, 175-184).*
Moustakas et al., Journal of Cell Science, 2001, 114:4359-4369.*
Scifinder_2018_US20050014942A1.*
Javelaud et al., Molecular Cancer, 2011, 10:2 (labeled pp. 1-14) (Year: 2011).*
Li et al., Diabetes, 2010, 59:2612-2624 (Year: 2010).*
Liu et al., Pharmaceutical Research, 2006, 23:82-89 (Year: 2006).*
Calone et al., "Inhibition of TGFβ3 Signaling and its Implications in Anticancer Treatments," Experimental Oncology, vol. 34, No. 1, Jan. 1, 2012, 9-16.
Medrano, "Repression of TGF-β Signaling by the Oncognic Piolein SKI in Human Melanomas: Consquences for Proliferatio, Survival, and Metastasis," Oncogene (2003) 22, 3123-3129.
Yanagisawa et al., "Induction of Apoptosis by Smad3 and down-regulation of Smad3 Expression in Response to TGF-β in human Normal Lung Epithelial Cells," Oncogene (1998) 17, 1743-1747.
Duke et al., "Regulation of Cell proliferation by Smad Proteins," Journal of Cellular Physiology, vol. 191, pp. 1-6 (2002).
Huang et al., American Journal of Physiology Endrocrinology and Metabolism, 2009, 296:E1344-E1353.
Jinnin et al., "Characterization of SIS3, a Novel Specific Inhibitor of Smad3,and Its Effect on Transforming Growth Factor-β 1-Induced Extracellular Matrix Expression", Mol. Pharmacol., vol. 69, No. 2, pp. 597-607 (2006).
Kocic et al., European Journal of Cancer, 2012, 48:155-1557, published online on Jul. 26, 2011.
Liu et al., "Effect of siRNA—mediated Smad3 silence on proliferation and spoptosis in activated hepatic stellate cells", Chinese Journal of Pathophysiology, vol. 27, No. 7, pp. 1376-1381 (2011).
Tsai et al., "TGF-β through Smad3 signaling stimulates vascular smooth muscle cell proliferation and neointimal formation", Am. J. Physiol. Heart Circ. Physiol, vol. 297, pp. H540-H549 (2009).
Vo et al., "Differential role of Sloan-Kettering Institute (Ski) protein in Nodal and transforming growth factor-beta (TGF-β)-induced Smad signaling in prostate cancer cells", Carcinogenesis, vol. 33, No. 11, pp. 2054-2064 (2012).
Zhang et al., PLOS One, 2011, 6:e20319, pp. 1-12.
International Search Report and Written Opinion dated Feb. 20, 2014 for International Patent Application No. PCT/CN2013/086053, 13 pages.

* cited by examiner

*Primary Examiner* — Alana Harris Dent
(74) *Attorney, Agent, or Firm* — Kilpatrick Townsend & Stockton LLP

(57) ABSTRACT

The present invention resides in the discovery that Smad3, a key downstream mediator of TGF-β signaling, plays a critical role in development and progression of cancer. Thus, this application provides for a novel method of treating cancer by inhibiting Smad3 signaling, such as through administration of SIS3, an inhibitor of Smad3. Further provided are compositions and kits useful for treating cancer by way of inhibiting Smad3 signaling.

10 Claims, 7 Drawing Sheets

Figure 2
A. Day 21 (Subcutaneous melanoma)
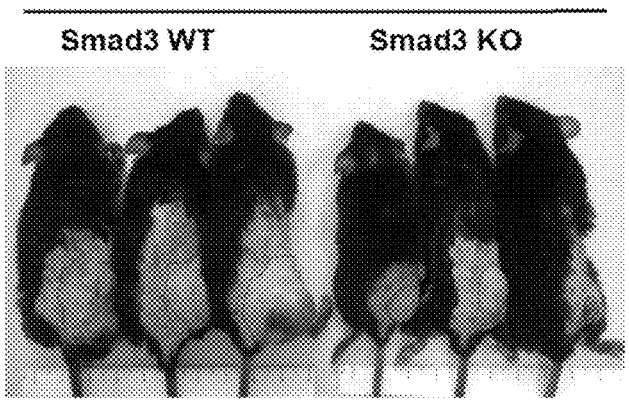
B. Tumor weight
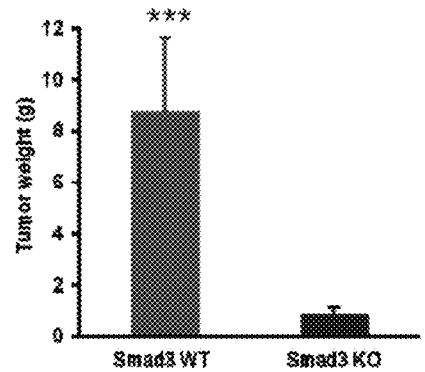
C. Tumor volume
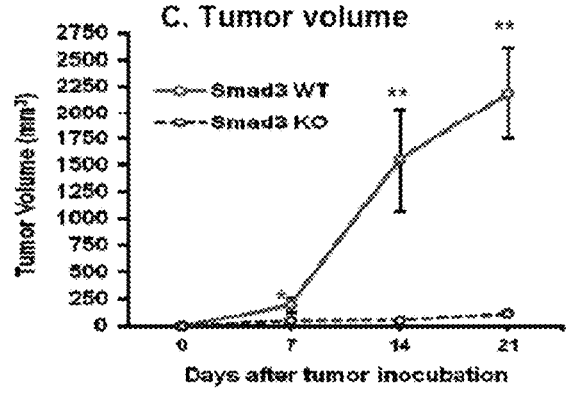
D. Survival rate
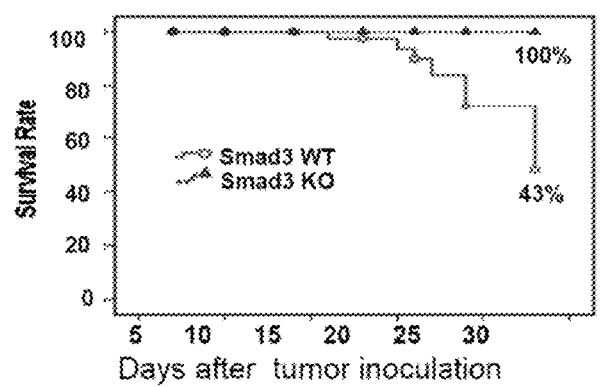
E. Lung metastatic melanoma (Day 21)
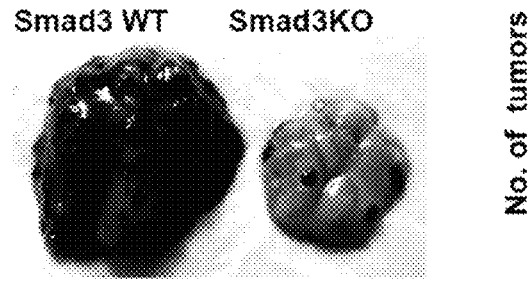
F. Lung metastatic tumor No. (Day 21)
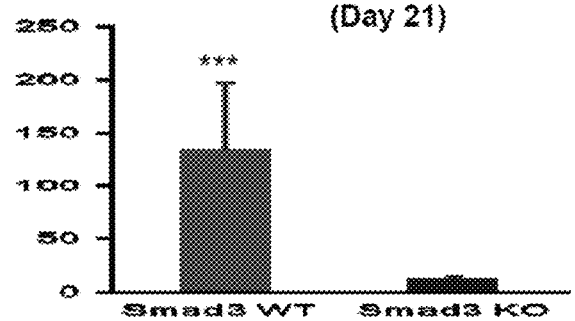

Figure 5
A. Tumor growth (B16F10 melanoma)
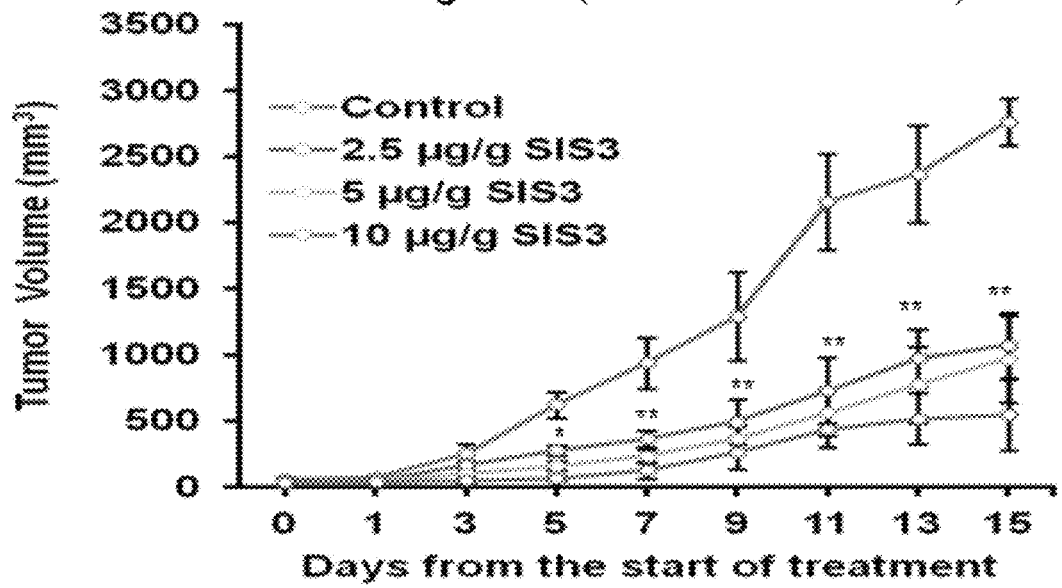
B. Survival rate (B16F10 melanoma)
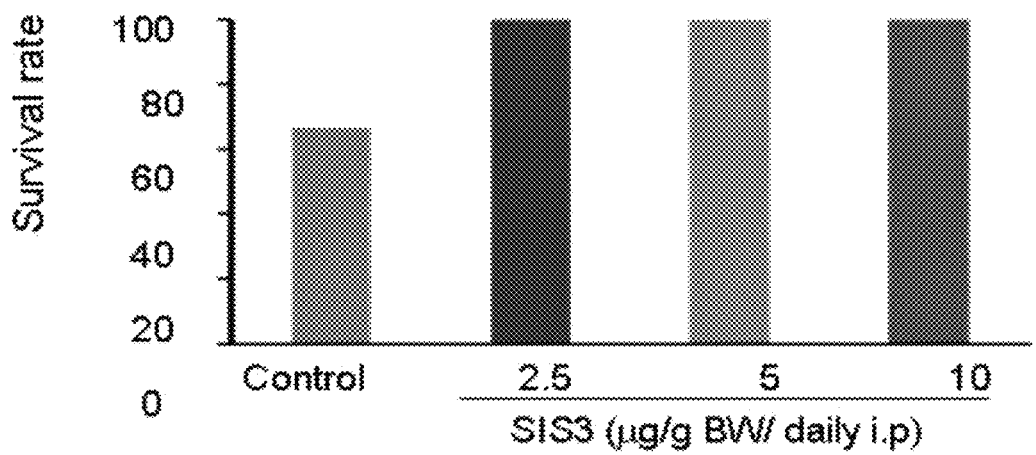
C. SIS3 prevents melanoma invasion and metastasis
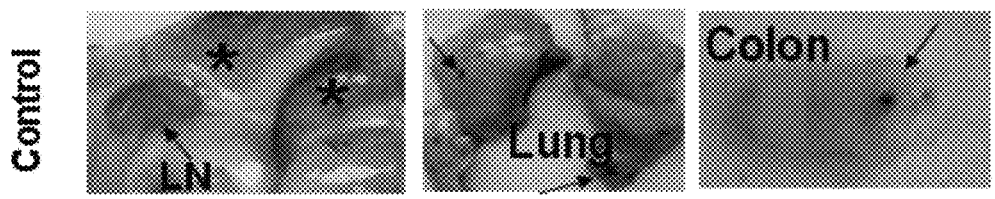

Figure 6
A. Tumor growth (LLC lung carcinoma)
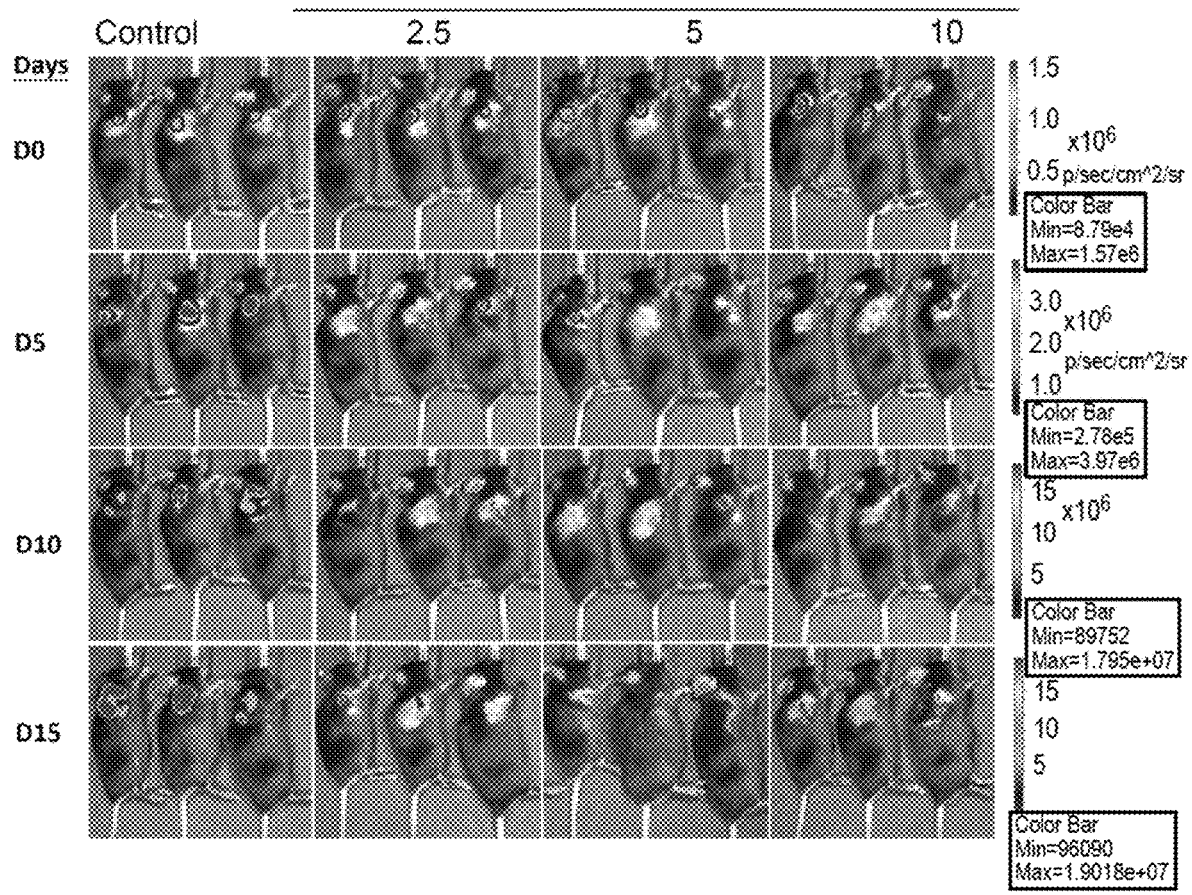
B. Tumor volume (LLC lung carcinoma)
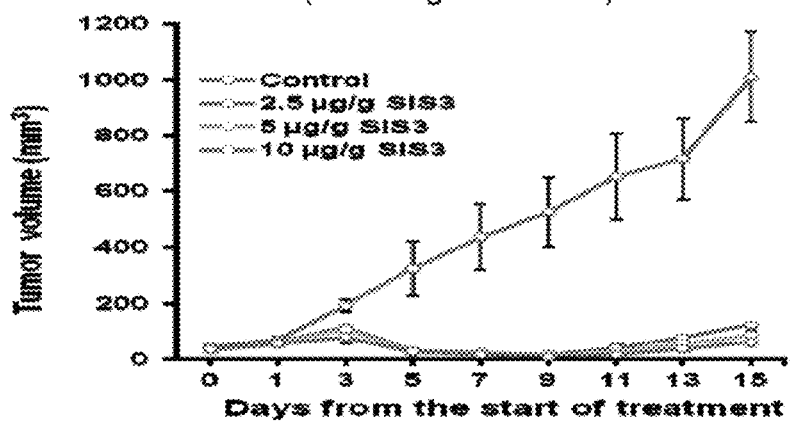

Figure 7
A. LLC lung cancer weight
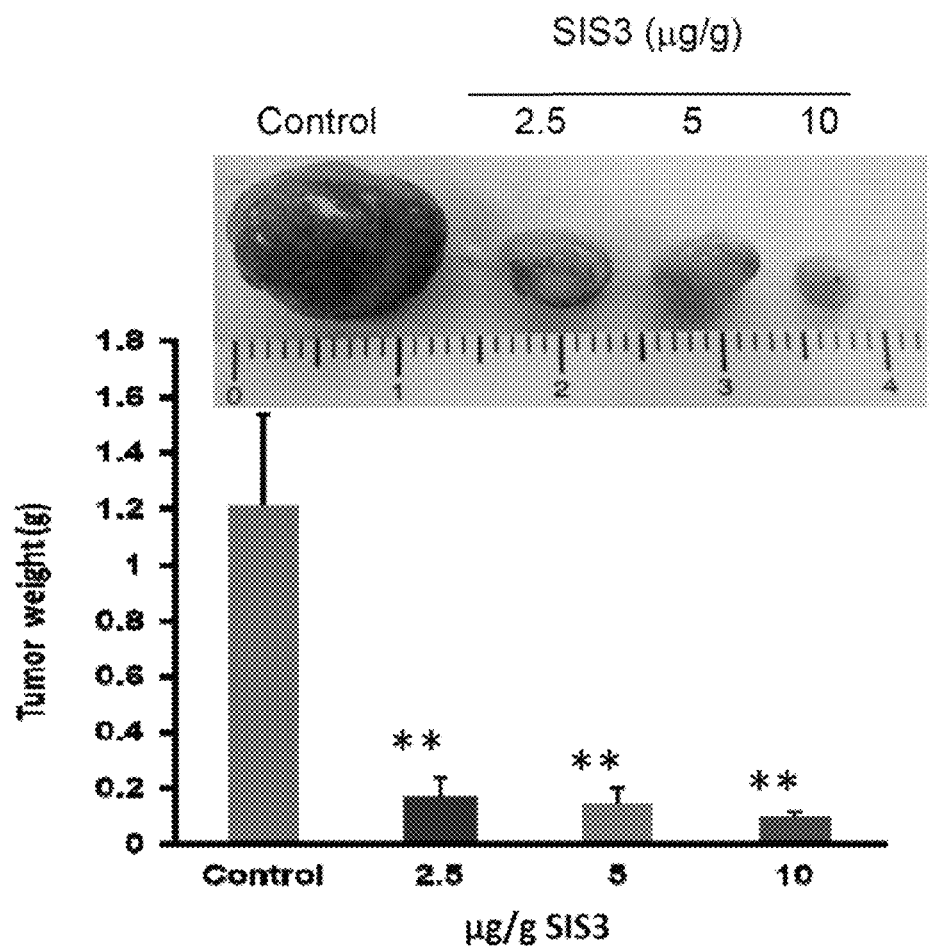
B. LLC lung cancer survival rate
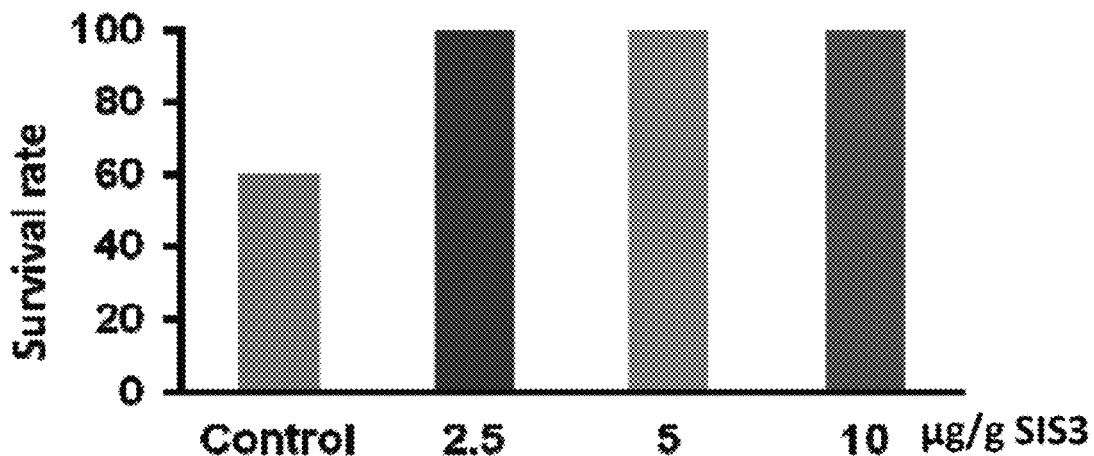

TREATMENT OF CANCER USING A SMAD3 INHIBITOR

RELATED APPLICATIONS

This application is a continuation of U.S. application Ser. No. 13/779,090, filed Feb. 27, 2013 which claims priority to U.S. Provisional Patent Application No. 61/719,114, filed Oct. 26, 2012, the contents of which are incorporated by reference in the entirety for all purposes.

BACKGROUND OF THE INVENTION

Cancer is a generic term for a large group of diseases that can affect any part of the body. One defining feature of cancer is the rapid proliferation of abnormal cells that grow beyond their usual boundaries. Cancer cells can then invade adjoining parts of the body and spread to other organs in a process known as metastasis. Metastasis is the main cause of death from cancer and can also be promoted by the cells surrounding the cancer called cancer stromal cells or cancer microenviroments.

According to the World Health Organization (WHO), cancer is a leading cause of death worldwide, accounting for 7.6 million deaths (around 13% of all deaths) in 2008. Lung, stomach, liver, colon and breast cancer cause the most cancer deaths each year. Despite intense research effort and technological advancement in biomedical sciences, deaths from cancer worldwide are projected to continue rising, with an estimated 13.1 million deaths in 2030.

Because of the prevalence of cancer and its significant impact on humanity, there remains an urgent need to develop new and more effective strategies for cancer treatment. The present invention addresses this and other related needs in that it provides a new anti-cancer treatment by using a Smad3 inhibitor to inhibit both cancer cell growth and supportive function of the cancer microenvironment.

BRIEF SUMMARY OF THE INVENTION

The invention relates to methods and compositions useful for inhibiting proliferation of a cell based on the discovery that the Smad3-mediated cellular signal transduction play a key role in the development and progression of cancer, especially the types that are responsive to TGF-β stimulation, including cancer cells and cancer stromal cells such as vascular endothelial cells, fibroblasts, neutrophils, eosinophils, mast cells, T cells and subsets, B cells, macrophages, and NK cells.

Thus, in the first aspect, the present invention provides a method for inhibiting proliferation of a cell, including but not limited to inhibiting cancer cell proliferation, tumor growth, invasion, and metastasis. The method includes the step of contacting the cell with an effective amount of an inhibitor of Smad3, which may be a small molecule inhibitor (such as SIS3 or another chemical, either synthetic or naturally occurring, e.g., a natural extract from herbs), or a macromolecule (such as an inactivating antibody against Smad3, a polypeptide, an siRNA, a microRNA, a miniRNA, an incRNA, or an antisense oligonucleotide). In some embodiments, the cell is a cancer cell, which may be within a human body. In some embodiments, the cancer is lung carcinoma or melanoma, including primary and metastatic cancers. Also targeted by the Smad3 inhibitor are various cells surrounding the cancer tissue or cancer stromal cells, i.e., cells in the cancer microenvironment of the primary or metastatic cancer in the human body, including vascular endothelial cells, fibroblasts, neutrophils, eosinophils, mast cells, T cells and subsets, B cells, macrophages, and NK cells within the cancer microenviroment. In some embodiments, the targeted cell is a metastatic cancer cell within the human body such as a cell in the lymph nodes, liver, lung, bone, kidney, brain, gastric, or colon tissues. In some embodiments, the contacting step may involve subcutaneous, intramuscular, intravenous, intraperitoneal, or oral administration. For example, the Smad3 inhibitor may be administered in the form of a solution, a powder, a paste/cream, a tablet, or a capsule.

In a second aspect, the present invention provides a composition useful for inhibiting cell proliferation, e.g., for treating cancer by suppressing cancer cell growth, and by blocking cancer supportive cells within the cancer microenvironment, thereby preventing cancer invasion and metastasis. The composition includes an effective amount of an inhibitor of Smad3 and a pharmaceutically acceptable excipient. In some cases, the composition is formulated for subcutaneous, intramuscular, intravenous, intraperitoneal, topical, or oral administration. For instance, the composition may be in the form of a solution, a powder, a paste/cream, a tablet, or a capsule.

In a third aspect, the present invention provides a kit for inhibiting proliferation of a cell, e.g., for treating cancer by suppressing cancer cell growth. The kit includes a container comprising the composition described above. In some embodiments, the composition is formulated for subcutaneous, intramuscular, intravenous, intraperitoneal, topical, or oral administration, e.g., the composition may be in the form of a solution, a powder, a paste/cream, a tablet, or a capsule. Optionally, the kit will further comprise an instruction manual for administration of the first and second compositions.

In a fourth aspect, the present invention provides methods for identifying Smad3 inhibitors. One of such methods is based on the physical interaction between Smad3 protein and the inhibitor and therefore comprises the steps: (1) contacting a Smad3 protein and a test compound, under conditions permissible for binding between Smad3 and a potential inhibitor; and (2) detecting the level of Smad3-test compound binding, wherein an increased level of binding above the non-specific background level or a negative control level indicates the test compound as a potential inhibitor of Smad3.

Another screening method is based on detection of direct inhibitory effect of a test compound on Smad3 signaling. Both in vitro and in vivo assays may be used. For example, cells expressing Smad3 and TGF-β receptor and thus responsive to TGF-β stimulation can be contacted with a test compound, proliferation/survival rate of the cells can then be monitored and compared to control cells that have not been contacted with the test compound. Suppressed cell growth rate or increased cell death is indication of a compound being a Smad3 inhibitor. Alternatively, downstream changes due to TGF-β signaling, e.g., increased phosphorylation of Smad3 protein, ERK1/2 activation, cyclin D1 expression, AKT and mTor activation can also be monitored to provide an indication whether a particular candidate compound may be a Smad3 inhibitor. Whenever suppressed signaling via Smad3 is observed, the test compound is identified as a potential inhibitor of Smad3.

When used in either of the above-described screening assay systems, the Smad3 protein may be recombinantly produced or endogenously expressed in a cell, and the assays may be conducted in a cell-free or whole cell-based environment. A compound that has been identified as a Smad3 inhibitor may be subject to further testing to confirm its inhibitory effect.

BRIEF DESCRIPTION OF THE DRAWINGS

FIG. 2. Mice lacking Smad3 are protected melanoma (B16F10) growth, invasion, metastasis, and death. Note that in contrast to Smad3 WT mice, Smad3 KO mice are protected against subcutaneous B16F10 cells (3 million cells/mouse) growth (A-C), invasion (not shown), metastasis and death (C). This is further confirmed by intravenous injection of B16F10 cells (3 million cells/mouse), showing that Smad3 KO mice largely prevent lung metastatic tumor formation (E and F). Results from this study demonstrate that Smad3-dependent microenvironments promote cancer growth, invasion, metastasis, and death. N=6.

FIG. 5. Smad3 inhibitor (SIS3) inhibits cancer growth (A) and prevents cancer from invasion and metastasis, and death (B) induced by subcutaneous melanoma (B16F10, 3 million cells/mouse) in a dosage-dependent manner in a syngeneic mouse model. Note that cancer invasion into the subcutaneous tissues or body muscles (*) and metastasis to lymph nodes (LN), lung, and colon are blunted by treatment with SIS3. N=5.

FIG. 6. SIS3 prevents LLC lung carcinoma growth. (A) Live imaging analysis, (B) quantitative analysis of tumor volume. Results show that Smad3 inhibitor (SIS3) inhibits lung carcinoma (LLC) growth in a dosage-dependent manner in a syngeneic mouse model. Note that most of cancers become undetectable after 10 days treatment with SIS3 at doses of 5-10 µg/g body weight. N=5

FIG. 7. Smad3 inhibitor (SIS3) prevents cancer growth as demonstrated by tumor weight (A) and the death (B) induced by subcutaneous lung carcinoma (LLC, 2 million cells/mouse) in a dosage-dependent manner in a syngeneic mouse model. N=5

DEFINITIONS

Figure 1:
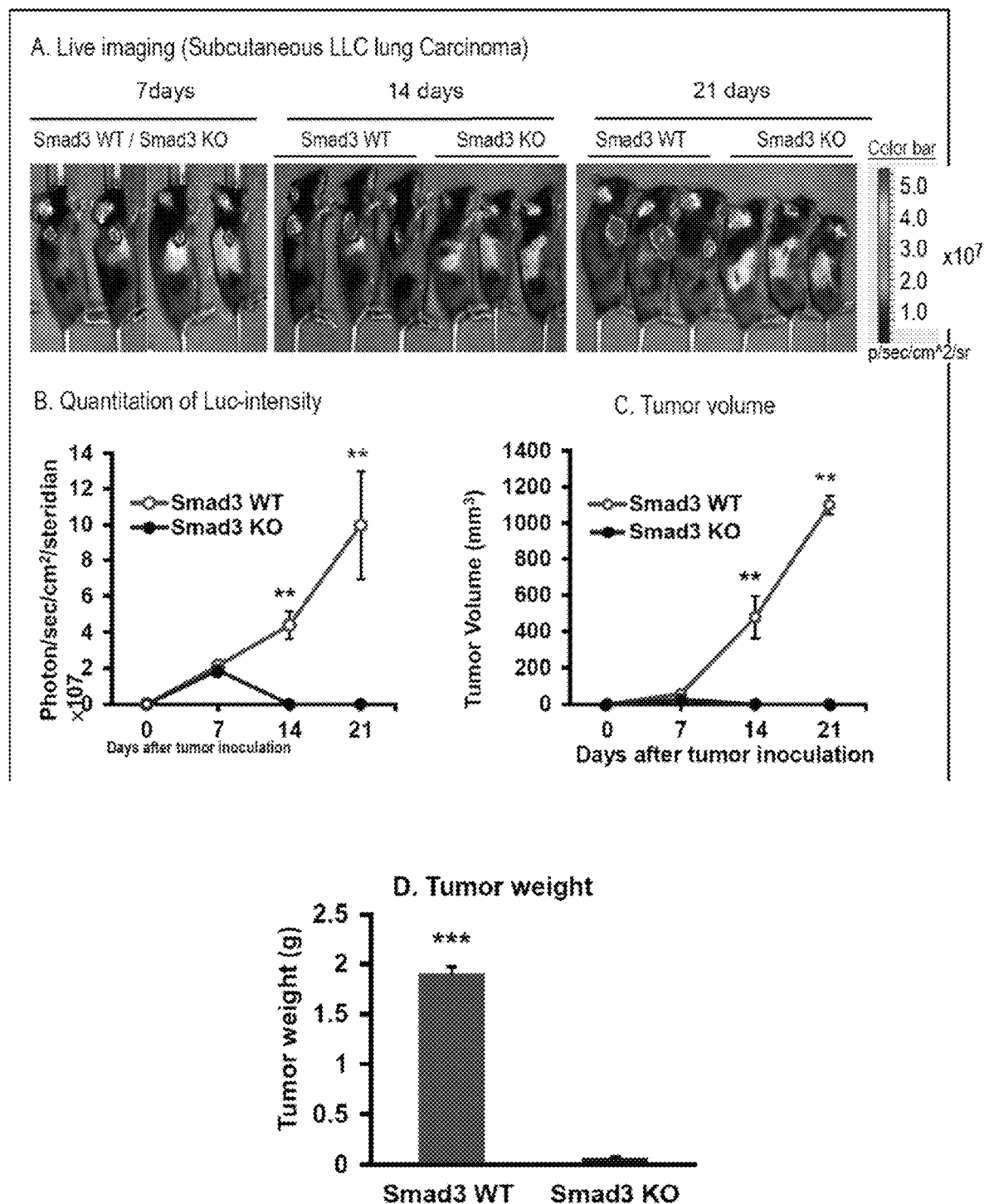
FIG. 1. Mice lacking Smad3 are protected against lung carcinoma (LLC) growth from day 14 onwards. Note that in contrast to Smad3 WT mice, no cancers are detectable in Smad3 KO mice by both live imaging (A,B), quantitative tumor volume (C), and tumor weight (D) at over days 14-21 after subcutaneous implantation of LLC cancer cells (3 million cells/mouse), indicating Smad3-dependent microenvironments determining cancer growth. N=6.
Figure 3:
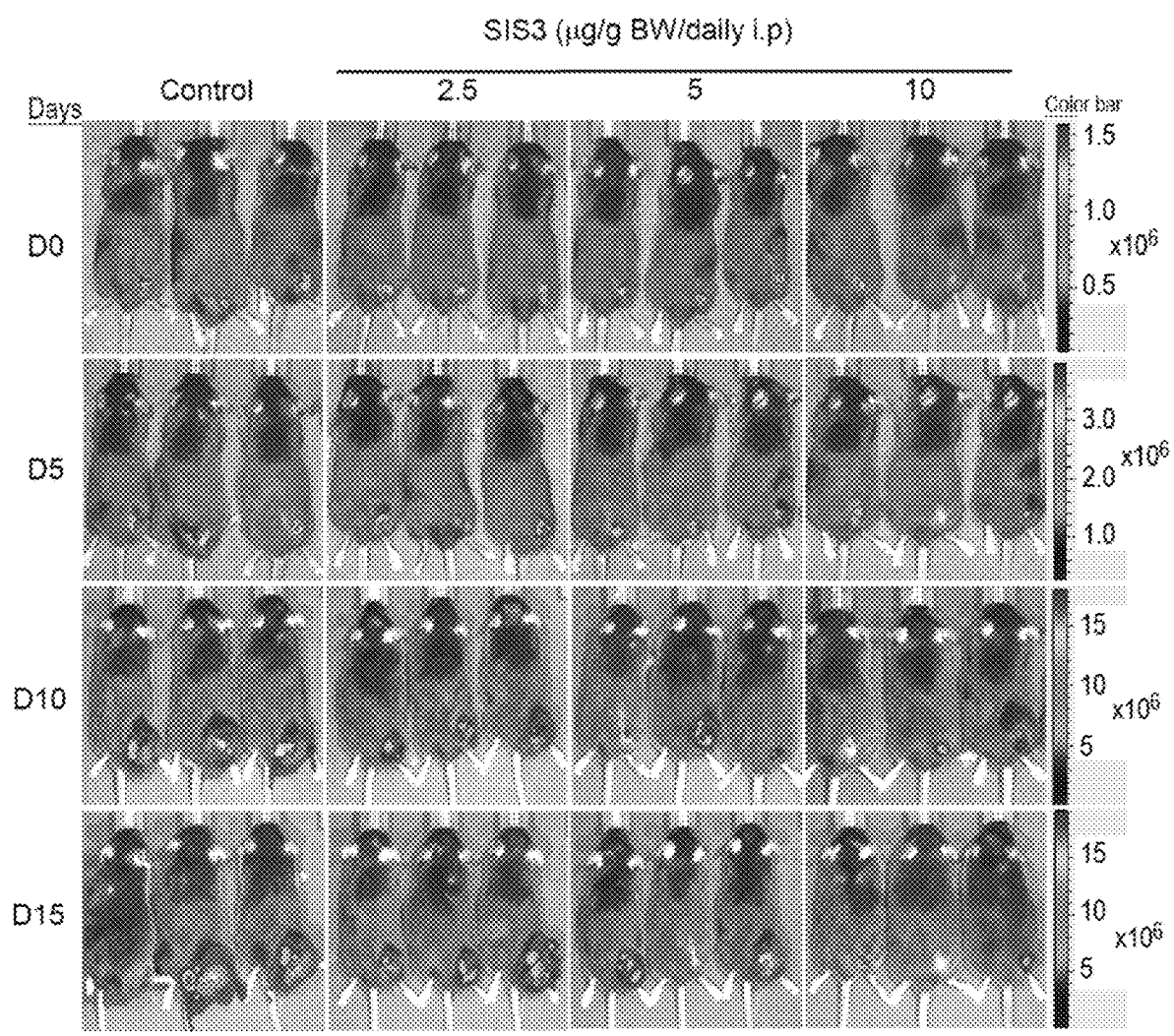
FIG. 3. Live imaging analysis shows that Smad3 inhibitor (SIS3) inhibits melanoma (B16F10) growth in a dosage-dependent manner in a syngeneic mouse model. N=5
Figure 4:
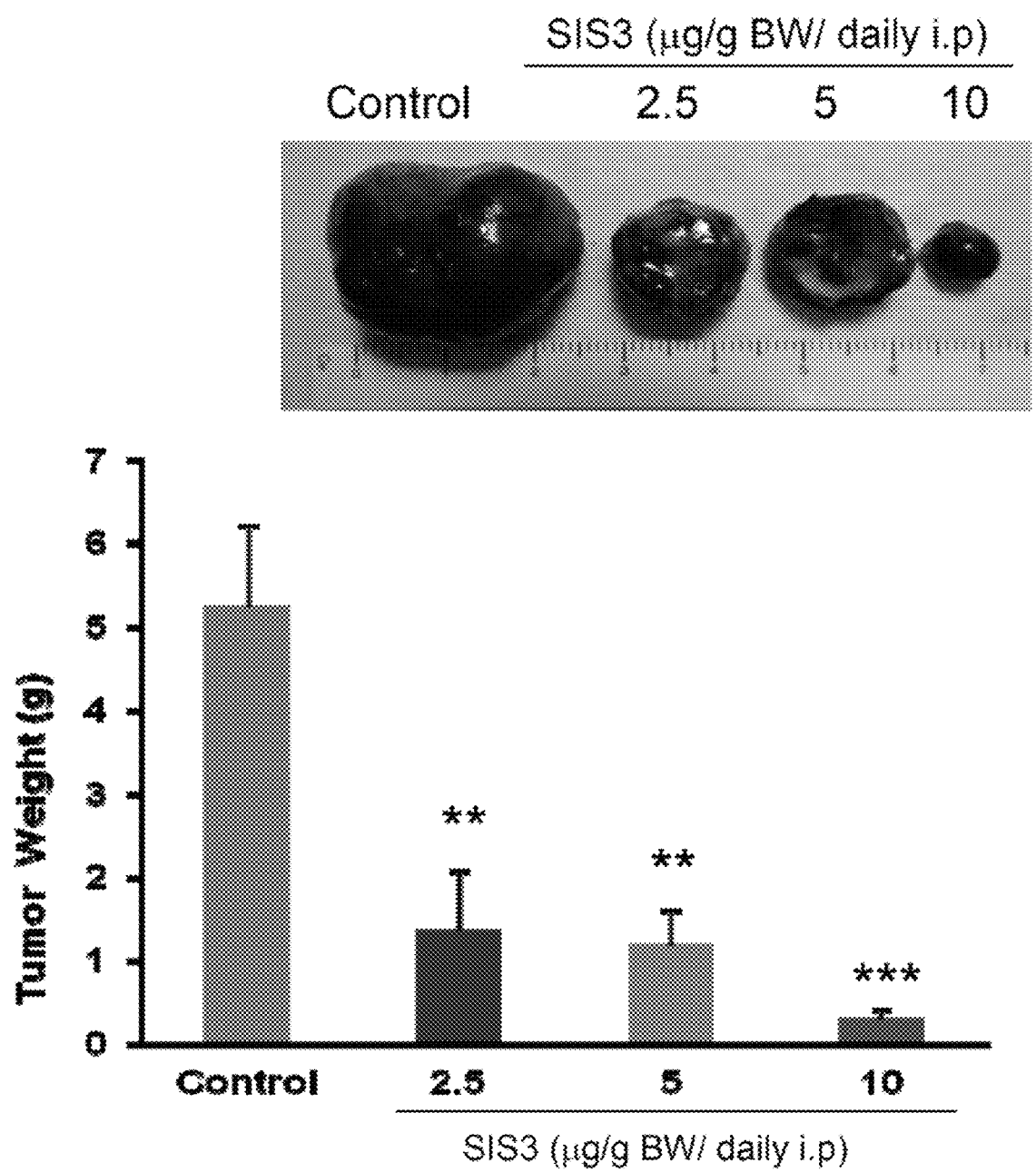
FIG. 4. Smad3 inhibitor (SIS3) inhibits cancer growth as demonstrated by markedly lowering the cancer weight in subcutaneous melanoma (B16F10, 3 million cells/mouse) in a dosage-dependent manner in a syngeneic mouse model. N=5

The term "inhibiting" or "inhibition," as used herein, refers to any detectable negative effect on a target biological process, such as cellular signal transduction, cell proliferation, tumorigenicity, and metastatic potential. Typically, an inhibition is reflected in a decrease of at least 10%, 20%, 30%, 40%, or 50% in target process (e.g., Smad3-mediated signaling or cancer proliferation), or any one of the downstream parameters mentioned above, when compared to a control.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The term "effective amount," as used herein, refers to an amount that produces therapeutic effects for which a substance is administered. The effects include the prevention, correction, or inhibition of progression of the symptoms of a disease/condition and related complications to any detectable extent. The exact amount will depend on the nature of the therapeutic agent, the manner of administration, and the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter.

An "antibody" refers to a polypeptide substantially encoded by an immunoglobulin gene or immunoglobulin genes, or fragments thereof, which specifically bind and recognize an antigen, for example, the Smad3 protein. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies may exist in various forms, e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology.

Further modification of antibodies by recombinant technologies is also well known in the art. For instance, chimeric antibodies combine the antigen binding regions (variable regions) of an antibody from one animal with the constant regions of an antibody from another animal. Generally, the antigen binding regions are derived from a non-human animal, while the constant regions are drawn from human antibodies. The presence of the human constant regions reduces the likelihood that the antibody will be rejected as foreign by a human recipient. On the other hand, "humanized" antibodies combine an even smaller portion of the non-human antibody with human components. Generally, a humanized antibody comprises the hypervariable regions, or complementarity determining regions (CDR), of a non-human antibody grafted onto the appropriate framework regions of a human antibody. Antigen binding sites may be wild type or modified by one or more amino acid substitutions, e.g., modified to resemble human immunoglobulin more closely. Both chimeric and humanized antibodies are made using recombinant techniques, which are well-known in the art (see, e.g., Jones et al. (1986) *Nature* 321:522-525).

Thus, the term "antibody," as used herein, also includes antibody fragments either produced by the modification of whole antibodies or antibodies synthesized de novo using recombinant DNA methodologies (e.g., single chain Fv, a chimeric or humanized antibody).

The term "SIS3," as used herein, refers to a cell-permeable, selective inhibitor of TGF-β1-dependent Smad3 phosphorylation and Smad3-mediated cellular signaling. It is a chemical having the molecular weight of 453.5, chemical name (6,7-Dimethoxy-2-((2E)-3-(1-methyl-2-phenyl-1H-pyrrolo[2,3-b]pyridin-3-yl-prop-2-enoyl))-1,2,3,4-tetrahydroisoquinoline), and chemical shown below:

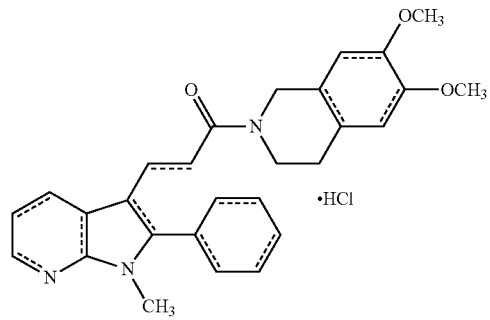

SIS3 may be synthesized from indole derivatives according to published methods of 2-(N-methylindolyl)acrylic acid, followed by condensation with the corresponding amine. See, e.g., Jinnin et al. 2006 *Mol. Pharmacol.* 69:597. SIS3 is also commercially available from various venders such as Santa Cruz, Sigma, and Millipore for the basic biological research purpose only.

DETAILED DESCRIPTION OF THE INVENTION

I. Introduction

Cancer remains one of the leading causes of human deaths. Cancer treatment with cytotoxic drugs is, however, frequently ineffective and presents high cytotoxicity with severe systemic side-effects. Increasing evidence shows that transforming growth factor-β (TGF-β) acts as a potent tumor promoter in established carcinoma. Cancer-derived TGF-β drives malignant progression by constitutively inducing epithelial to mesenchymal transition and tumor-associated angiogenesis, and by suppressing anti-tumor immunity in cancer microenvironment. Based that information, many therapeutic approaches by targeting TGF-β receptors using soluble TGF-β receptor II, small molecule ALK5 kinase inhibitors, as well as neutralizing antibodies, have been developed by researchers and pharmaceutical companies. Some of them have been shown promise in early pre-clinical studies, including SD-093, SD-208, and SM16. However, TGF-β is a fundamental anti-inflammatory cytokine and general blockade of TGF-β at the level of TGF-β receptor is also problematic due to the likelihood of causing autoimmune diseases. Thus, research into the downstream of TGF-β signaling to identify more specific therapeutic targets related to cancer progression may offer a better anticancer therapy clinically.

A new discovery from a recent study by the inventor's group was that mice null for Smad3, a key downstream mediator of TGF-β signaling, are protected against cancer growth, invasion, metastasis (for example, to lymph nodes, liver, lung, gastric, and colon tissues), and death in two highly invasive cancer models including lung carcinoma (LLC) and melanoma (B16F10). This finding indicates that Smad3-dependent cancer microenvironment in the host determines the cancer progression or regression. This also indicates that targeting Smad3 on the cancer microenvironment (as well as cancer) may offer a better anticancer therapy. A study was performed to test this new therapeutic strategy by targeting Smad3 with a Smad3 inhibitor (SIS3) in established melanoma (B16F10) in mice. Similarly to the results seen in Smad3 KO mice, treatment with SIS3 virtually suppressed cancer growth, invasion, and metastasis, and prevented the cancer death. Thus, SIS3 is a novel anticancer drug by targeting TGF-β/Smad3, which is highly clinically relevant and may result in a novel, safer, and more effective anticancer therapy.

II. General Recombinant Technology

Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of a gene of interest, a polynucleotide encoding a polypeptide of interest, and synthetic oligonucleotides can be verified after cloning or subcloning using, e.g., the chain termination method for sequencing double-stranded templates of Wallace et al., *Gene* 16: 21-26 (1981).

III. Identification of Inhibitors for Smad3-Mediated Signaling

Inhibitors of Smad3 activity can be of virtually any chemical and structural nature: they may be polypeptides, polynucleotides, and small molecules. As long as they possess confirmed inhibitory effect against Smad3 as a downstream signal transduction mediator of TGF-β, such inhibitors may be useful for inhibiting cancer cell proliferation and therefore useful for treating cancer.

A. Smad3 Binding Assays

An in vitro assay can be used to screen for potential inhibitors of Smad3 signaling based in the binding between Smad3 and a candidate compound. Once a compound is identified in the binding assay, further testing may be conducted to confirm and verify the compounds capability to inhibiting Smad3-mediated signaling. In general, such an assay can be performed in the presence of a Smad3 protein or a fragment thereof, for example, a recombinantly produced Smad3 protein or fragment, under conditions permitting its binding to a potential binding partner. For convenience, the Smad3 protein or the candidate compound may be immobilized onto a solid support and/or labeled with a detectable moiety. A third molecule, such as an antibody (which may include a detectable label) to Smad3 protein, can also be used to facilitate detection.

In some cases, the binding assays can be performed in a cell-free environment; whereas in other cases, the binding assays can be performed within a cell or on the cell surface, for example, using cells recombinantly or endogenously expressing an appropriate Smad3 polypeptide.

B. Smad3 Phosphorylation Assays

The inhibitors of Smad3-mediated cellular signaling are useful for their ability to inhibit TGF-β signaling, especially as anti-cancer therapeutics for patients suffering from cancer exacerbated by TGF-β signaling. Assays for confirming such inhibitory effect of an inhibitor can be performed in vitro or in vivo. An in vitro assay typically involves exposure of cultured cells to an inhibitor and monitoring of subsequent biological and biochemical changes in the cells. For example, following exposure to an inhibitor at 0.1-20 μg/ml for 0.5-48 hours, suitable cells (such as those expressing Smad3, TGF-β receptor and responsive to TGF-β stimulation) are examined for their proliferation/survival status using methods such as direct cell number counting, BrdU or $H^3$-thymidine incorporation, tetrazolium salt 3,[4,5-dimethylthiazol-2-yl]-2,5-diphenyltetrazolium bromide (MTT) cell proliferation assay, 3-(4,5-dimethylthiazol-2-yl)-5-(3-carboxymethoxyphenyl)-2-(4-sulfophenyl)-2H-tetrazolium (MTS) cell proliferation assay, chicken embryo allantoic membrane (CAM) assay, TUNNEL assay, annexin V binding assay, etc. Further downstream changes due to TGF-β signaling, e.g., phosphorylation of Smad3 protein, ERK1/2 activation, cyclin D1 expression, and AKT activation can also be monitored to provide an indication of suppressed signaling via Smad3. In addition, tumorigenicity and/or metastic potential of cancer cells are also useful parameters for monitoring and can be tested by methods such as colony formation assays or soft agar assays. An inhibitory effect is detected when a decrease in Smad3-mediated signaling, as indicated by any one aforementioned parameter, of at least 10%, 20%, 30%, 40%, 50%, 60%, 70%, 80%, 90% or more is observed.

The anti-cancer effects of a Smad3 signaling inhibitor of the present invention can also be demonstrated in in vivo assays. For example, a Smad3 inhibitor can be injected into animals that have a compromised immune system (e.g., nude mice, SCID mice, or NOD/SCID mice) and therefore permit xenograft tumors. Injection methods can be subcutaneous, intramuscular, intravenous, intraperitoneal, or intratumoral in nature. Tumors development is subsequently monitored by various means, such as measuring tumor volume and scoring secondary lesions due to metastases, in comparison with a control group of animals with similar tumors but not given the inhibitor. The Examples section of this disclosure provides detailed description of some exemplary in vivo assays. An inhibitory effect is detected when a negative effect on tumor growth or metastasis is established in the test group. Preferably, the negative effect is at least a 10% decrease; more preferably, the decrease is at least 20%, 30%, 40%, 50%, 60%, 70%, 80%, or 90%.

As stated above, Smad3 inhibitors can have diverse chemical and structural features. For instance, an inhibitor can be a non-functional Smad3 mutant that retaining the binding ability Smad3 to its upstream or downstream signaling molecules, an antibody to Smad3 that interferes with Smad3-mediated signaling, or any small molecule or macromolecule that simply hinders the interaction between Smad3 and its upstream or downstream signaling molecules. Essentially any chemical compound can be tested as a potential inhibitor of Smad3 signaling. Most preferred are generally compounds that can be dissolved in aqueous or organic (especially DMSO-based) solutions. Inhibitors can be identified by screening a combinatorial library containing a large number of potentially effective compounds. Such combinatorial chemical libraries can be screened in one or more assays, as described herein, to identify those library members (particular chemical species or subclasses) that display a desired characteristic activity. The compounds thus identified can serve as conventional "lead compounds" or can themselves be used as potential or actual therapeutics.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)) and carbohydrate libraries (see, e.g., Liang et al., *Science,* 274:1520-1522 (1996) and U.S. Pat. No. 5,593,853). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with β-D-glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and benzodiazepines, U.S. Pat. No. 5,288,514).

IV. Pharmaceutical Compositions and Administration

The present invention also provides pharmaceutical compositions or physiological compositions comprising an effective amount of a compound that inhibits Smad3-mediated signaling and therefore inhibits cancer development, such as a dominant negative Smad3 mutant or its encoding nucleic acid, a nucleic acid encoding an antisense or miRNA, miniRNA, long non-coding RNA targeting Smad3, an inactivating anti-Smad3 antibody, small chemicals, peptides, proteins, natural extract compounds from herbs, or SIS3, in both prophylactic and therapeutic applications. Such pharmaceutical or physiological compositions also include one or more pharmaceutically or physiologically acceptable excipients or carriers. Pharmaceutical compositions of the invention are suitable for use in a variety of drug delivery systems. Suitable formulations for use in the present invention are found in *Remington's Pharmaceutical Sciences,* Mack Publishing Company, Philadelphia, Pa., 17th ed. (1985). For a brief review of methods for drug delivery, see, Langer, Science 249: 1527-1533 (1990).

The pharmaceutical compositions of the present invention can be administered by various routes, e.g., oral, subcutaneous, transdermal, intramuscular, intravenous, or intraperitoneal. The preferred routes of administering the pharmaceutical compositions are local delivery to an organ or tissue suffering from a condition exacerbated by TGF-β/Smad3 mediated signaling (e.g., intratumor injection to a tumor) at daily doses of about 0.01-2500 mg, preferably 2.5-500 mg, of a Smad3 inhibitor for a 70 kg adult human per day. The appropriate dose may be administered in a single daily dose or as divided doses presented at appropriate intervals, for example as two, three, four, or more subdoses per day.

For preparing pharmaceutical compositions containing a Smad3 inhibitor such as SIS3, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., SIS3. In tablets, the active ingredient (an inhibitor of TGF-β/Smad3 signaling) is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient of an inhibitor of Smad3-mediated signaling. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active compound of a Smad3 inhibitor with encapsulating material as a carrier providing a capsule in which the inhibitor (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., a Smad3 inhibitor such as SIS3) or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., a Smad3 signaling inhibitor) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 to 8.

The pharmaceutical compositions containing a Smad3 inhibitor can be administered for prophylactic and/or therapeutic treatments. In therapeutic applications, compositions are administered to a patient already suffering from a condition that may be exacerbated by the TGF-β/Smad3 mediated cellular signaling in an amount sufficient to prevent, cure, reverse, or at least partially slow or arrest the symptoms of the condition and its complications, such as the onset, progression, and metastasis of certain types of cancer. An amount adequate to accomplish this is defined as a "therapeutically effective dose." Amounts effective for this use will depend on the severity of the disease or condition and the weight and general state of the patient, but generally range from about 0.1 mg to about 2,500 mg of the inhibitor per day for a 70 kg patient, with dosages of from about 2.5 mg to about 500 mg of the inhibitor per day for a 70 kg patient being more commonly used.

In prophylactic applications, pharmaceutical compositions containing a Smad3 inhibitor are administered to a patient susceptible to or otherwise at risk of developing a disease or condition in which excessive TGF-β/Smad3 mediated signaling is undesirable, in an amount sufficient to delay or prevent the onset of the symptoms. Such an amount is defined to be a "prophylactically effective dose." In this use, the precise amounts of the inhibitor again depend on the patient's state of health and weight, but generally range from about 0.1 mg to about 2,500 mg of the inhibitor for a 70 kg patient per day, more commonly from about 2.5 mg to about 500 mg for a 70 kg patient per day.

Single or multiple administrations of the compositions can be carried out with dose levels and pattern being selected by the treating physician. In any event, the pharmaceutical formulations should provide a quantity of a Smad3 inhibitor sufficient to effectively inhibit cellular signaling mediated by Smad3 in the patient, either therapeutically or prophylatically.

V. Therapeutic Applications Using Nucleic Acids

A variety of cancers can be treated by therapeutic approaches that involve introducing a nucleic acid encoding a polypeptide inhibitor of Smad3 signaling or small oligonucleotide sequence (such as antisense or miRNA) into a cell such that the coding sequence is transcribed and the polypeptide or oligonucleotide inhibitor is produced in the cell. Types of cancers amenable to treatment by this approach include a broad spectrum of solid tumors, the survival and growth of which rely on to some extent the continue signaling of TGF-β/Smad3. For discussions on the application of gene therapy towards the treatment of genetic as well as acquired diseases, see, Miller *Nature* 357:455-460 (1992); and Mulligan *Science* 260:926-932 (1993).

A. Vectors for Gene Delivery

For delivery to a cell or organism, a polynucleotide encoding a polypeptide that inhibits Smad3 signaling (such as a dominant negative mutant of Smad3 or an inactivation Smad3 antibody) or encoding an inhibitory oligonucleotide (such as antisense or miRNA) can be incorporated into a vector. Examples of vectors used for such purposes include expression plasmids capable of directing the expression of the nucleic acids in the target cell. In other instances, the vector is a viral vector system wherein the polynucleotide is incorporated into a viral genome that is capable of transfecting the target cell. In one embodiment, the encoding polynucleotide can be operably linked to expression and control sequences that can direct expression of the polypeptide or oligonucleotide in the desired target host cells. Thus, one can achieve expression of the polypeptide or oligonucleotide inhibitor under appropriate conditions in the target cell.

B. Gene Delivery Systems

Viral vector systems useful in the expression of a polypeptide or oligonucleotide inhibitor of Smad3-mediate cellular signaling include, for example, naturally occurring or recombinant viral vector systems. Depending upon the particular application, suitable viral vectors include replication competent, replication deficient, and conditionally replicating viral vectors. For example, viral vectors can be derived from the genome of human or bovine adenoviruses, vaccinia virus, herpes virus, adeno-associated virus, minute virus of mice (MVM), HIV, sindbis virus, and retroviruses (including but not limited to Rous sarcoma virus), and MoMLV. Typically, the coding sequence of interest (e.g., one encoding for a polypeptide or oligonucleotide inhibitor of the present invention) are inserted into such vectors to allow packaging of the gene construct, typically with accompanying viral DNA, followed by infection of a sensitive host cell and expression of the coding sequence of interest.

As used herein, "gene delivery system" refers to any means for the delivery of a polynucleotide sequence of the invention to a target cell. In some embodiments of the invention, nucleic acids are conjugated to a cell receptor ligand for facilitated uptake (e.g., invagination of coated pits and internalization of the endosome) through an appropriate linking moiety, such as a DNA linking moiety (Wu et al., *J. Biol. Chem.* 263:14621-14624 (1988); WO 92/06180), or by ultrasound-microbubble delivery system (Lan H Y et al., *J. Am Soc. Nephrol.* 14:1535-1548). For example, nucleic acids can be linked through a polylysine moiety to asialo-oromucocid, which is a ligand for the asialoglycoprotein receptor of hepatocytes.

Similarly, viral envelopes used for packaging gene constructs that include the nucleic acids of the invention can be modified by the addition of receptor ligands or antibodies specific for a receptor to permit receptor-mediated endocytosis into specific cells (see, e.g., WO 93/20221, WO 93/14188, and WO 94/06923). In some embodiments of the invention, the DNA constructs of the invention are linked to viral proteins, such as adenovirus particles, to facilitate endocytosis (Curiel et al., *Proc. Natl. Acad. Sci. U.S.A.* 88:8850-8854 (1991)). In other embodiments, molecular conjugates of the instant invention can include microtubule inhibitors (WO/9406922), synthetic peptides mimicking influenza virus hemagglutinin (Plank et al., *J. Biol. Chem.* 269:12918-12924 (1994)), and nuclear localization signals such as SV40 T antigen (WO93/19768).

Retroviral vectors may also be useful for introducing the coding sequence of a polypeptide or oligonucleotide inhibitor of the invention into target cells or organisms. Retroviral vectors are produced by genetically manipulating retroviruses. The viral genome of retroviruses is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild type retroviral genome and the proviral DNA have three genes: the gag, the poi and the env genes, which are flanked by two long terminal repeat (LTR) sequences. The gag gene encodes the internal structural (nucleocapsid) proteins; the poi gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site) (see, Mulligan, In: *Experimental Manipulation of Gene Expression*, Inouye (ed), 155-173 (1983); Mann et al., *Cell* 33:153-159 (1983); Cone and Mulligan, *Proceedings of the National Academy of Sciences, U.S.A.*, 81:6349-6353 (1984)).

The design of retroviral vectors is well known to those of ordinary skill in the art. In brief, if the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including, e.g., European Patent Application EPA 0 178 220; U.S. Pat. No. 4,405,712, Gilboa *Biotechniques* 4:504-512 (1986); Mann et al., *Cell* 33:153-159 (1983); Cone and Mulligan *Proc. Natl. Acad. Sci. USA* 81:6349-6353 (1984); Eglitis et al. *Biotechniques* 6:608-614 (1988); Miller et al. *Biotechniques* 7:981-990 (1989); Miller (1992) supra; Mulligan (1993), supra; and WO 92/07943.

The retroviral vector particles are prepared by recombinantly inserting the desired nucleotide sequence into a retrovirus vector and packaging the vector with retroviral capsid proteins by use of a packaging cell line. The resultant retroviral vector particle is incapable of replication in the host cell but is capable of integrating into the host cell genome as a proviral sequence containing the desired nucleotide sequence. As a result, the patient is capable of producing, for example, a polypeptide or polynucleotide of the invention and thus restore the cells to a normal phenotype.

Packaging cell lines that are used to prepare the retroviral vector particles are typically recombinant mammalian tissue culture cell lines that produce the necessary viral structural proteins required for packaging, but which are incapable of producing infectious virions. The defective retroviral vectors that are used, on the other hand, lack these structural genes but encode the remaining proteins necessary for packaging. To prepare a packaging cell line, one can construct an infectious clone of a desired retrovirus in which the packaging site has been deleted. Cells comprising this construct will express all structural viral proteins, but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available in the prior art. Examples of these cell lines include Crip, GPE86, PA317 and PG13 (see Miller et al., *J. Virol.* 65:2220-2224 (1991)). Examples of other packaging cell lines are described in Cone and Mulligan *Proceedings of the National Academy of Sciences, USA,* 81:6349-6353 (1984); Danos and Mulligan *Proceedings of the National Academy of Sciences, USA,* 85:6460-6464 (1988); Eglitis et al. (1988), supra; and Miller (1990), supra.

Packaging cell lines capable of producing retroviral vector particles with chimeric envelope proteins may be used. Alternatively, amphotropic or xenotropic envelope proteins, such as those produced by PA317 and GPX packaging cell lines may be used to package the retroviral vectors.

C. Pharmaceutical Formulations

When used for pharmaceutical purposes, the nucleic acid encoding a polypeptide or oligonucleotide Smad3 inhibitor is generally formulated in a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al. *Biochemistry* 5:467 (1966).

The compositions can additionally include a stabilizer, enhancer or other pharmaceutically acceptable carriers or vehicles. A pharmaceutically acceptable carrier can contain a physiologically acceptable compound that acts, for example, to stabilize the nucleic acids of the invention and any associated vector. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. Examples of carriers, stabilizers or adjuvants can be found in Remington's *Pharmaceutical Sciences*, Mack Publishing Company, Philadelphia, Pa., 17th ed. (1985).

D. Administration of Formulations

The formulations containing a polynucleotide sequence encoding a polypeptide or oligonucleotide inhibitor of Smad3 can be delivered to any tissue or organ using any delivery method known to the ordinarily skilled artisan. In some embodiments of the invention, the encoding polynucleotide sequences are formulated for subcutaneous, intramuscular, intravenous, intraperitoneal, or intratumor injection, or for oral ingestion or for topical application.

The formulations containing the nucleic acid of the invention are typically administered to a cell. The cell can be provided as part of a tissue, such as an epithelial membrane, or as an isolated cell, such as in tissue culture. The cell can be provided in vivo, ex vivo, or in vitro.

The formulations can be introduced into the tissue of interest in vivo or ex vivo by a variety of methods. In some embodiments of the invention, the nucleic acids of the invention are introduced into cells by such methods as microinjection, calcium phosphate precipitation, liposome fusion, ultrasound, electroporation, or biolistics. In further embodiments, the nucleic acids are taken up directly by the tissue of interest, for example, when the targeted tissue is the skin.

In some embodiments of the invention, the nucleic acids of the invention are administered ex vivo to cells or tissues explanted from a patient, then returned to the patient. Examples of ex vivo administration of therapeutic gene constructs include Nolta et al., *Proc Natl. Acad. Sci. USA* 93(6):2414-9 (1996); Koc et al., *Seminars in Oncology* 23(1):46-65 (1996); Raper et al., *Annals of Surgery* 223(2): 116-26 (1996); Dalesandro et al., *J. Thorac. Cardi. Surg.*, 11(2):416-22 (1996); and Makarov et al., *Proc. Natl. Acad. Sci. USA* 93(1):402-6 (1996).

Effective dosage of the formulations will vary depending on many different factors, including means of administration, target site, physiological state of the patient, and other medicines administered. Thus, treatment dosages will need to be titrated to optimize safety and efficacy. In determining the effective amount of the vector to be administered, the physician should evaluate the particular nucleic acid used, the disease state being diagnosed; the age, weight, and overall condition of the patient, circulating plasma levels, vector toxicities, progression of the disease, and the production of anti-vector antibodies. The size of the dose also will be determined by the existence, nature, and extent of any adverse side-effects that accompany the administration of a particular vector. To practice the present invention, doses of SIS3 ranging from about 0.1 µg-100 mg per patient are typical. Doses generally range between about 0.01 and about 100 µg per kilogram of body weight, preferably between about 0.1 and about 50 µg/kg of body weight or about $10^8$-$10^{10}$ or $10^{12}$ particles per injection. In general, the dose equivalent of a naked nucleic acid from a vector is from about 1-100 µg for a typical 70 kg patient, and doses of vectors which include a retroviral particle are calculated to yield an equivalent amount of nucleic acid encoding a polypeptide or oligonucleotide that inhibits Smad3-mediated signal transduction.

VI. Kits

The invention also provides kits for inhibiting Smad3 signaling and therefore for treating cancer according to the method of the present invention. The kits typically include a container that contains (1) a pharmaceutical composition having an effective amount of an inhibitor of Smad3-mediated signaling (for instance, a dominant negative Smad3 mutant, a polynucleotide sequence encoding the mutant polypeptide, a polynucleotide encoding an antisense or miRNA against Smad3, an inactivating antibody of Smad3, or a small molecule inhibitor of Smad3 such as SIS3) and (2) informational material containing instructions on how to dispense the pharmaceutical composition, including description of the type of patients who may be treated (e.g., cancer patients with excessive TGF-β/Smad3 signaling), the schedule (e.g., dose and frequency) and route of administration, and the like.

EXAMPLES

The following examples are provided by way of illustration only and not by way of limitation. Those of skill in the art will readily recognize a variety of non-critical parameters that could be changed or modified to yield essentially the same or similar results.

Example 1

SIS3 Treatment of Lung Carcinoma and Melanoma

Therapeutic effect of SIS3 was tested in subcutaneously invasive mouse model of lung carcinoma and melanoma. Lucifase-labeled highly invasive mouse lung carcinoma cells (LLC-luc) and melanoma cells (B16F10-luc) were injected subcutaneously into genetically-identical C57/BL6 mice at a dose of 2 million cells in 200 ul PBS per mouse. Cancer growth, invasion, and metastasis were monitored by measuring tumor size, weight, and bioluminescent imaging weekly. After cancer was established at one week after implantation, tumor-bearing mice received intraperitoneally SIS3 at dosages of 2.5, 5, and 10 ug/Kg body weight daily for 2 weeks. Control animals received daily saline, instead of SIS3, and a group of tumor-bearing mice without any treatment (used as untreated controls) were also monitored. Five mice per group were used in this study. Mice were weighed and tumor size or metastasis was examined by live bioluminescent imaging weekly. The survival rate was recorded. All mice were euthanized 2 weeks after treatment for further examination by histology and tumor volume and weight, invasion, and metastasis.

This study provides evidence supporting a new anticancer therapy by targeting TGF-β/Smad3 with a Smad3 inhibitor (SIS3). As shown in FIGS. 1 and 2, mice null for Smad3 were protected against cancer growth, invasion, metastasis, and death in two highly invasive cancer models including lung carcinoma (LLC) and melanoma (B16F10). Results from these studies clearly demonstrated that Smad3-dependent microenvironments determined and promoted cancer growth, invasion, metastasis, and death, providing strong evidence for the development of a novel anticancer therapy by using Smad3 inhibitor. This was developed by this invention that treatment with a Smad3 inhibitor (SIS3) suppressed, in both lung carcinoma (LLC) and melanoma (B16F10), cancer growth and invasion into the cancer surrounding tissues, and metastatsis to lymph nodes, lung, liver, gastric and colon tissue in a dosage-dependent manner, and therefore prevented the cancer death (FIGS. 3-7). Thus, the present invention indicates SIS3 as a novel and effective anticancer agent by way of regulating cellular signal transduction mediated by TGF-β/Smad3.

All patents, patent applications, and other publications, including GenBank Accession Numbers, cited in this application are incorporated by reference in the entirety for all purposes.

What is claimed is:

1. A method for inhibiting proliferation of a lung carcinoma or melanoma cell within a human body, comprising the step of contacting the cell with an effective amount of an inhibitor of Smad3, wherein the inhibitor is 6,7-dimethoxy-2-((2E)-3-(1-methyl-2-phenyl-1H-pyrrolo[2,3-b]pyridin-3-yl-prop-2-enoyl))-1,2,3,4-tetrahydroisoquinoline (SIS3) or an analog thereof.

2. The method of claim 1, wherein the inhibitor is 6,7-dimethoxy-2-((2E)-3-(1-methyl-2-phenyl-1H-pyrrolo[2,3-b]pyridin-3-yl-prop-2-enoyl))-1,2,3,4-tetrahydroisoquinoline (SIS3).

3. The method of claim 1, wherein the contacting step comprises injection or oral administration.

4. The method of claim 3, wherein the injection is subcutaneous, intramuscular, intravenous, intraperitoneal, or intratumoral injection.

5. A method of treating lung carcinoma or melanoma in a human subject in need thereof, the method comprising administering to the subject a composition comprising an effective amount of an inhibitor of Smad3, wherein the inhibitor is SIS3 or analog thereof.

6. The method of claim 5, wherein the inhibitor is SIS3.

7. The method of claim 5, wherein the administering step comprises injection or oral administration.

8. The method of claim 7, wherein the injection is subcutaneous, intramuscular, intravenous, intraperitoneal, or intratumoral injection.

9. The method of claim 5, wherein the composition is in the form of a solution, a powder, a paste, a tablet, or a capsule.

10. The method of claim 5, wherein the composition consists of the inhibitor of Smad3 and one or more pharmaceutically acceptable excipients.

* * * * *